United States Patent [19]

Chorvat et al.

[11] Patent Number: 4,500,708

[45] Date of Patent: Feb. 19, 1985

[54] BENZOTHIAZINE DERIVATIVES

[75] Inventors: Robert J. Chorvat, Arlington Heights; George R. Lenz; Suzanne Evans Radak, both of Glenview, all of Ill.

[73] Assignee: G. D. Serle & Co., Skokie, Ill.

[21] Appl. No.: 602,782

[22] Filed: Apr. 23, 1984

[51] Int. Cl.$^3$ .......................................... C07D 513/04
[52] U.S. Cl. ....................................................... 544/34
[58] Field of Search ........................................ 544/34

[56] References Cited

U.S. PATENT DOCUMENTS

| | | |
|---|---|---|
| 3,118,884 | 1/1964 | Clarke ..................................... 544/34 |
| 3,389,136 | 6/1968 | Clarke ..................................... 544/34 |
| 4,223,136 | 9/1980 | Chorvat .................................. 544/34 |
| 4,356,302 | 10/1982 | Chorvat et al. ...................... 544/34 |

Primary Examiner—John M. Ford
Attorney, Agent, or Firm—Steven M. Odre

[57] ABSTRACT

The present invention relates to a class of novel annulated 4H-1,4-benzothiazine derivatives. The invention further relates to pharmaceutical compositions containing such annulated benzothiazine derivatives and to the use of such compounds and compositions as anorectic agents. In particular, certain of the novel annulated 4H-1,4-benzothiazine derivatives are effective anorectic agents when administered orally.

13 Claims, No Drawings

BENZOTHIAZINE DERIVATIVES

BACKGROUND OF THE INVENTION

Various annulated 4H-1,4-benzothiazine derivatives have been known to possess anorectic activity. In particular, U.S. Pat. No. 4,356,302 and U.S. Pat. No. 4,399,279 disclose a class of annulated 4H-1,4 benzothiazine derivatives which possess appetite suppressive properties and when administered produce a decrease in food consumption and a weight loss.

SUMMARY OF THE INVENTION

The present invention relates to a class of novel compounds of the formula

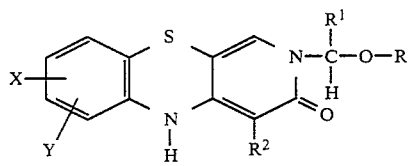

wherein
R is hydrogen or a

group wherein $R^3$ is $C_1$–$C_{15}$ alkyl;

$R^1$ is hydrogen or $C_1$–$C_3$ alkyl;

$R^2$ is phenyl or substituted phenyl containing one or two substituents selected from the class consisting of halo, hydroxy, trifluoromethyl, methoxy, cyano and $C_1$–$C_4$ alkyl; and X and Y are independently hydrogen, halo, nitro, trifluoromethyl, amino or $C_1$–$C_4$ alkoxy.

The invention further relates to pharmaceutical compositions containing the compounds of formula (I) and to the use of such compounds and compositions as anorectic agents.

DETAILED DESCRIPTION OF THE INVENTION

The $C_1$–$C_3$ alkyl radicals represented by $R^1$ include straight chain or branched chain hydrocarbon moieties containing up to three carbon atoms. Illustrative alkyl radicals include methyl, ethyl, propyl and isopropyl.

The term "halo" as used herein refers to fluoro, chloro, bromo and iodo. The term "substituted phenyl" as used herein represents a substituted phenyl radical preferably containing one or two substituents. Among these substituents include $C_1$–$C_4$ alkyl, hydroxy, trifluoromethyl, methoxy, cyano or halo, preferably chloro or bromo. The substituents of the substituted phenyl moieties represented by $R^2$ are preferably halo and most prefrably chloro. Positioning of the substituents on the phenyl relative to the point of attachment of the phenyl, or, where two are present, to each other is not critical. Thus, within the scope of this invention are o-, m-, or p-monosubstituted phenyls of the type described above, such as o-fluorophenyl, p-chlorophenyl, m-trifluoromethylphenyl, p-bromophenyl, p-hydroxyphenyl and 2,4-, 2,6-, and 3,4-disubstituted phenyls of the type described above, such as 2,4-dichlorophenyl, 2,6-dichlorophenyl and 3,4-dichlorophenyl. The substituted phenyl moieties are preferably mono-substituted and more preferably substituted in the para position.

The $C_1$–$C_{15}$ alkyl radicals represented by $R^3$ include straight chain or branched chain hydrocarbon moieties containing up to fifteen carbon atoms. Illustrative alkyl radicals include methyl, ethyl, propyl, isopropyl, butyl, isobutyl, sec-butyl, tert-butyl, pentyl, neopentyl, hexyl, isohexyl, heptyl, decyl and like monovalent, saturated acyclic, straight- or branched-chain hydrocarbon groupings of the empirical formula $$-C_pH_{(2p+1)}$$

wherein p represents an integer of less than 16. The preferred alkyl radicals represented by $R^3$ contain from one to six and more preferably from 2 to 4 and most preferably three carbon atoms.

A preferred embodiment of the present invention comprises a class of compounds according to formula (I) wherein X, Y and $R^1$ are hydrogen and $R^2$ is halophenyl. A more preferred embodiment of the present invention comprises a class of compounds according to formula (I) wherein X, Y, $R^1$ and R are hydrogen and $R^2$ is 4-chlorophenyl. Another more preferred embodiment of the present invention comprises a class of compounds according to formula (I) wherein X, Y and $R^1$ are hydrogen, $R^2$ is 4-chlorophenyl and R is a

group wherein $R^3$ is a straight chain $C_1$–$C_4$ alkyl.

The compounds of the present invention may be prepared in accordance with the following general procedure:

A suspension comprising a 4-aryl-5H-pyrido[3,4-b][1,4]benzothiazin-3(2H)-one of the formula,

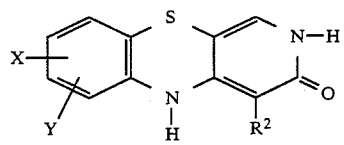

wherein X, Y and $R^2$ are above defined, in a suitable solvent such as dimethylformamide, is reacted with a base and the resulting mixture is heated on a steam bath until a solution forms. To this solution is added an aldehyde of the formula,

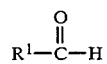

wherein $R^1$ is above defined, and the resulting reaction mixture is heated on a steam bath until formation of a solid product, an 4-aryl-2-hydroxyalkyl-5H-pyrido[3,4-b][1,4]benzothiazin-3(2H)-one, having the general formula

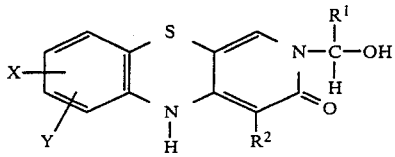

The 4-aryl-2-hydroxyalkyl-5H-pyrido[3,4-b][1,4]benzothiazin-3(2H)-one of formula (IV) is suspended under basic conditions in a suitable solvent, such as pyridine, and then reacted with an anhydride of the formula,

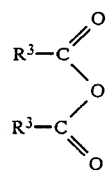

wherein $R^3$ is above defined, at room temperature for a period of from 1 to 2 hours to yield, upon the addition of water to the reaction mixture, a product having the general formula

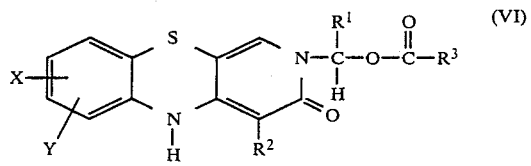

The 4-aryl-5H-pyrido[3,4-b][1,4]benzothiazin-3(2H)-one compounds utilized as starting materials in the above general procedure may be prepared in accordance with the procedure described in U.S. Pat. No. 4,356,302 and U.S. Pat. No. 4,399,279.

The compounds of the present invention are useful because they possess valuable pharmacological properties. In particular the compounds are anorectic agents. The anorectic utility of the compounds may be demonstrated by showing a dose responsive decrease in food intake and subsequent weight loss upon administration of the compounds to a subject.

The compounds of the present invention may be administered by any suitable route, preferably in the form of a pharmaceutical composition adapted to such route and in a dose effective for the treatment intended.

Accordingly, the invention provides a class of novel pharmaceutical compositions comprising one or more compounds of the present invention in association with one or more non-toxic pharmaceutically acceptable carriers and/or diluents and/or adjuvants and if desired other active ingredients. The composition may for example be administered orally or by injection.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain from about 5 to 250 mg, preferably from about 25 to 150 mg, of the active ingredient. A suitable daily dose for a patient may vary widely depending on the condition of the patient and other factors. However, a dose of from about 0.1 to 300 mg/kg body weight, preferably from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg per kg body weight injected per day in multiple doses depending on the disease being treated. A preferred daily dose would be from about 1 to 30 mg/kg body weight.

As indicated, the appropriate dose administered and the treatment regimen will be dependent, for example, on the severity of the condition thereof, on the route of administration, on the patient being treated and his response to treatment, and therefore may be widely varied.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved in water, polyethylene glycol, propylene glcyol, ethanol, corn oil, cottonseed oil, peanut oil, sesame oil, benzyl alcohol, sodium chloride, and/or various buffers. Other adjuvants and modes of administration are well and widely known in the parmaceutical art; see, for example, F. W. Martin et al., Remington's Pharmaceutical Sciences, 14th ed., Merck Publishing Co., Eaton, Pa., 1965.

The following examples describe in detail compounds illustrative of the present invention and methods which have been devised for their preparation. It will be apparent to those skilled in the art that many modifications, both of materials and of methods, may be practiced without departing from the purpose and intent of this disclosure.

EXAMPLE 1

To 5.0 g. of 4-(4-chlorophenyl)-5H-pyrido[3,4-b][1,4]benzothiazin-3-(2H)-one (15.3 mmol.) in 50 ml. of dimethylformamide was added 30 ml. of a 5% sodium hydroxide solution (37.5 mmol.), and the resulting suspension was heated on a steam bath until a solution formed. To the solution was then added 50 ml. of a 36% formaldehyde solution (60.0 mmol.), and the resulting reaction mixture was heated until a yellow precipitate formed. The hot reaction mixture was filtered, and the precipitate was washed well with water and dried under high vacuum at room temperature to yield 4-(4-chlorophenyl)-2-(hydroxymethyl)-5H-pyrido[3,4-b][1,4]benzothiazin-3(2H)-one complexed with water (4:1) as a yellow powder (5.15 g.; 93% yield) having the structural formula,

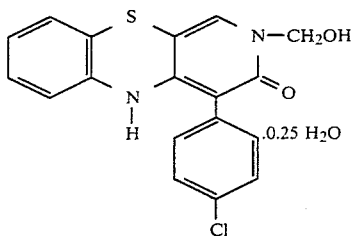

a melting point of greater than 300° C. and the following elemental analysis:

C$_{18}$H$_{13}$N$_2$O$_2$SCl.O.25H$_2$O: Calculated: C,59.83; H,3.77; N,7.75; Cl,9.81; Found: C,59.86; H,3.68; N,8.01; Cl,10.02.

EXAMPLE 2

To 1.0 g of 4-(4-chlorophenyl)-2-(hydroxymethyl-5H-pyrido[3,4-b][1,4]benzothiazin-3(2H)-one (2.8 mmol.) in 10 ml. of pyridine was added 2.5 ml. of butyric anhydride (15.3 mmol.) and the resulting suspension was stirred at room temperature for about 90 minutes. To the resulting solution was then added approximately twice the volume of water, resulting in the formation of a yellow precipitate. The mixture was filtered, and the collected yellow precipitate was washed with water, followed by diethyl ether, and then dried under high vacuum at room temperature to yield 4-(4-chlorophenyl)-2-[(1-oxobutoxy)methyl]-5H-pyrido[3,4-b][1,4]benzothiazin-3-(2H)-one as yellow needles (0.989 g; 83% yield) having the structural formula,

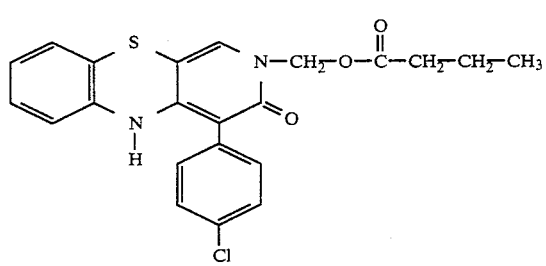

a melting point in the range of 158°–160° C. and the following elemental analysis:

C$_{22}$H$_{19}$N$_2$O$_3$SCl: Calculated: C,61.90; H,4.49; N,6.56; Cl,8.30; Found: C,61.70; H,4.62; N,6.30; Cl,8.35.

EXAMPLE 3

To 1.0 g of 4-(4-chlorophenyl)-2-(hydroxymethyl)-5H-pyrido[3,4-b][1,4]benzothiazin-3(2H)-one (2.8 mmol.) in 10 ml. of pyridine was added 5 ml. of valeric anhydride (25.5 mmol.) and the resulting suspension was stirred at room temperature for about 90 minutes. To the resulting solution was then added approximately twice the volume of water, resulting in the formation of a yellow precipitate, which was collected and purified using flash chromatography on silica gel, using 100% chloroform as the eluent. Fractions containing the product were combined, and the product was recrystallized from chloroform/methanol, then dried under high vacuum at 110° C. to yield 4-(4-chlorophenyl)-2-[(1-oxopentoxy)methyl]-5H-pyrido[3,4-b][1,4]benzothiazin-3(2H)-one complexed with chloroform (10:1) as yellow needles (0.632 g; 51% yield) having the structural formula,

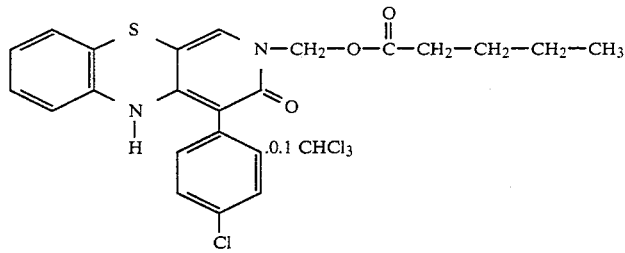

a melting point in the range of 175°–176° C. and the following elemental analysis:

C$_{23}$H$_{21}$N$_2$O$_3$SCl.O.1CHCl$_3$: Calculated: C,61.26; H,4.70; N,6.19; Cl,10.18; Found: C,61.07; H,4.75; N,6.10; Cl,10.09.

EXAMPLE 4

To 1.0 g. of 4-(4-chlorophenyl)-2-(hydroxymethyl)-5H-pyrido[3,4-b][1,4]benzothiazin-3(2H)-one (2.8 mmol.) in 8 ml. of pyridine was added 4 ml. of acetic anhydride (42.3 mmol.), and the resulting suspension was stirred at room temperature for about 1 hour. The resulting solution was then concentrated under a nitrogen atmosphere, and the residue was titurated with methanol to yield a yellow precipitate which was washed with methanol and then air-dried to yield 4-(4-chlorophenyl)-2-[(acetyloxy)methyl]-5H-pyrido[3,4-b][1,4]-benzothiazin-3(2H)-one as a yellow solid (0.65 g; 58% yield) having the structural formula,

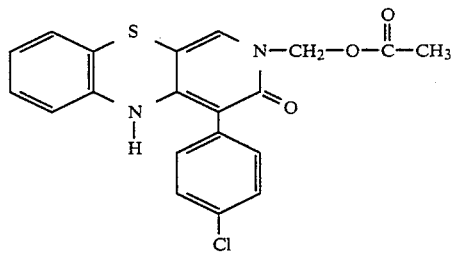

a melting point in the range of 119°–120° C. and the following elemental analysis:

C$_{20}$H$_{15}$N$_2$O$_3$SCl: Calculated: C,60.23; H,3.79; N,7.02; Cl,8.89; Found: C,59.94; H,3.72; N,6.97; Cl,8.86.

EXAMPLE 5

To 5.0 g. of 7-chloro-4-(4-chlorophenyl)-5H-pyrido[3,4-b][1,4]-benzothiazin-3(2H)-one (13.8 mmol.) in 50 ml. dimethylformamide was added 30 ml. of a 5% sodium hydroxide solution (37.5 mmol.) and the resulting suspension was heated on a steam bath until the solid dissolved. To the resulting solution was then added 50 ml. of 36% formaldehyde solution (60.0 mmol.), and the resulting reaction mixture was heated on a steam bath for 30 minutes, then cooled to room temmperature, yielding a yellow precipitate. The mixture was filtered, and the collected precipitate was washed with water and dried under vacuum at room temperature to yield 7-chloro-4-(4-chlorophenyl)-2-(hydroxymethyl)-5H-pyrido[3,4-b][1,4]benzothiazin-3(2H)-one as a yellow solid (4.7 g.; 87% yield) having the structural formula,

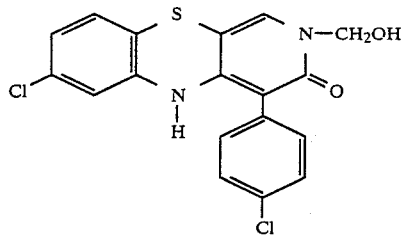

a melting point of 295°–300° C. (with decomposition) and the following elemental analysis:

$C_{18}H_{12}N_2O_2SCl_2$: Calculated: C,55.26; H,3.09; N,7.16; Found: C,55.39; H,3.07; N,7.32.

EXAMPLE 6

To 2.5 g. of 7-chloro-4-(4-chlorophenyl)-2-(hydroxymethyl)-5H-pyrido[3,4-b][1,4]benzothiazin-3(2H)-one (6.5 mmol.) in 30 ml. of pyridine was added 6.5 ml. of butyric anhydride (39.8 mmol.), and the resulting suspension was stirred at room temperature for about 90 minutes. The resulting solution was then poured onto an ice-water mixture resulting in the formation of a yellow precipitate, which was collected and washed with water. The precipitate was purified using flash chromatography on silica gel, using a mixture of 5% ethyl acetate: 95% methylene chloride as the eluent. Fractions containing the product were combined and triturated with ether to yield 7-chloro-4-(4-chlorophenyl)-2-[(1-oxobutoxy)methyl]-5H-pyrido[3,4-b][1,4]benzothiazin-3(2H)-one as a yellow crystalline solid (1.9 g; 64% yield) having the structural formula, a melting point in the range of 227°–229° C. and the following elemental analysis:

$C_{22}H_{18}N_2O_3SCl_2$: Calculated: C,57.27; H,3.93; N,6.07; Found: C,57.16; H,3.94; N,6.08.

EXAMPLE 7

A mixture of 3.0 g. of 5,5-dimethylhexanoic acid (23.0 mmol.) and 2.5 ml. of thionyl chloride (34.3 mmol.) was allowed to stand at room temperature for 16 hours. Upon addition of 20 ml. of Skellysolve B, the resulting solution was refluxed for 1 hour, then the solvent was removed in vacuo. The remaining residue was azeotroped twice with Skellysolve B to yield a pale yellow liquid which was added dropwise to a suspension of 3.0 g. of 4-(4-chlorophenyl)-2-(hydroxymethyl)-5H-pyrido[3,4-b][1,4]benzothiazin-3(2H)-one (8.4 mmol.) in 30 ml. of cold pyridine. After stirring in an ice-bath for 35 minutes, the reaction mixture was poured onto ice-water resulting in the formation of a solid product which was filtered, washed with water, and purified using flash chromatography on silica gel, using a mixture of 5% ethyl acetate: 95% methylene chloride as the eluent. Fractions containing product were combined and triturated with diethyl ether to yield 4-(4-chlorophenyl)-2-[(5,5-dimethyl-1-oxohexyloxy)methyl]-5H-pyrido[3,4-b][1,4]-benzothiazin-3(2H)-one as a yellow solid (2.4 g; 59% yield) having the structural formula, a melting point in the range of 143°–145° C. and the following elemental analysis:

$C_{26}H_{27}N_2O_3SCl$: Calculated: C,64.65; H,5.63; N,5.80; Found: C,64.85; H,5.70; N,5.85.

EXAMPLE 8

To 2.5 g. of 4-(4-chlorophenyl)-2-(hydroxymethyl)-5H-pyrido[3,4-b][1,4]benzothiazin-3(2H)-one (7.0 mmol.) in 25 ml. of pyridine at 0° C. was added 2.5 ml. of isovalery chloride (20.5 mmol.). After stirring for 35 minutes, the mixture was poured onto ice-water and allowed to stand for 16 hours at room temperature. The crude product which formed as an orange precipitate was collected, washed with water, air-dried, and purified using flash chromatography on silica gel, using a mixture of 5% ethyl acetate: 95% methylene chloride as the eluent. Fractions containing the product were combined and triturated with ether to yield 4-(4-chlorophenyl)-2-[(3-methyl-1-oxobutoxy)methyl]-5H-pyrido-[3,4-b][1,4]benzothiazin-3(2H)-one as a yellow solid (1.1 g; 36% yield) having the structural formula,

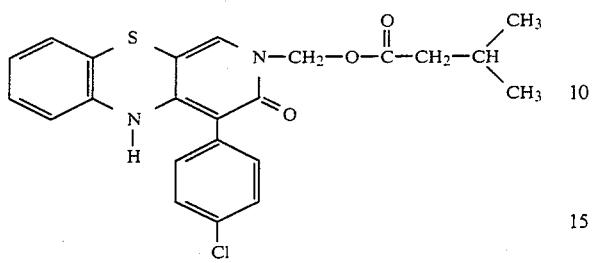

a melting point in the range of 163°-171° C. and the following elemental analysis:

$C_{23}H_{21}N_2O_3SCl$: Calculated: C,62.65; H,4.80; N,6.35; Found: C,61.85; H,4.73; N,6.23.

EXAMPLE 9

To 1.0 g of 4-(4-chlorophenyl)-2-(hydroxymethyl)-5H-pyrido[3,4-b][1,4]benzothiazin-3(2H)-one (2.8 mmol.) in 10 ml. of pyridine was added 5 ml. of trimethylacetic anhydride (46.5 mmol.), and the suspension was stirred at room temperature for 2.5 hours. To the resulting solution was then added enough water to precipitate the product, which was collected by filtration, washed with ether, and dried under high vacuum at room temperature to yield 4-(4-chlorophenyl)-2-[(2,2-dimethyl-1-oxopropoxy)methyl]-5H-pyrido[3,4-b][1,4]benzothiazin-3(2H)-one as a pale crystalline solid (1.0 g; 81% yield) having the structural formula,

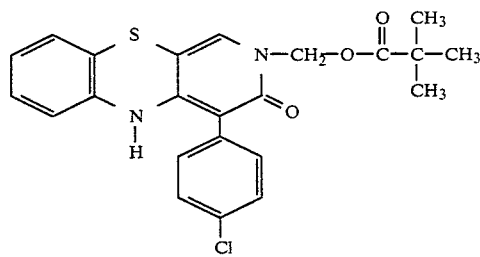

a melting point in the range of 208°-210° C. and the following elemental analysis:

$C_{23}H_{21}N_2O_3SCl$: Calculated: C,62.65; H,4.80; N,6.35; Cl,8.04; Found: C,62.65; H,4.79; N,6.35; Cl,7.97.

EXAMPLE 10

To 3.0 g. of 4-(4-chlorophenyl)-2-(hydroxymethyl)-5H-pyrido[3,4-b][1,4]benzothiazin-3(2H)-one (8.4 mmol.) suspended in 30 ml. of pyridine at 0° C. was added dropwise 2.5 ml. of hexadecanoyl chloride (10.9 mmol.). After stirring for 45 minutes, the mixture was poured onto ice-water and allowed to stand for 16 hours at room temperature, resulting in the formation of a yellow precipitate. The precipitate was collected, washed with water and air-dried, then purified using flash chromatography on silica gel, using a mixture of 5% ethyl acetate: 95% methylene chloride as the eluent. Fractions containing the product were combined, and the solvent was removed in vacuo. The residue was triturated with diethyl ether to yield 4-(4-chlorophenyl)-2-[(1-oxohexadecyloxy)methyl]-5H-pyrido[3,4-b][1,4]benzothiazin-3(2H)-one as a light yellow solid (1.69 g; 34% yield) having the structural formula,

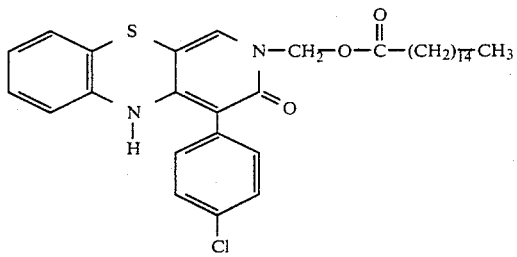

a melting point in the range of 89°-92° C. and the following elemental analysis:

$C_{34}H_{43}N_2O_3SCl$: Calculated: C,68.68; H,7.28; N,4.71; Found: C,68.57; H,7.27; N,4.75.

EXAMPLE 11

A mixture of 1.4 g. of 2-methylhexanoic acid (10.8 mmol.) and 3 ml. of thionyl chloride (41.1 mmol.) in 20 ml. of Skellysolve B was refluxed on a steam bath for five hours. The mixture was then concentrated under reduced pressure and the residue azeotroped twice with 30 ml. of cyclohexane to yield a colorless oil. The oil was then added dropwise to a cold, stirred suspension of 1.2 g. of 7-chloro-4-(4-chlorophenyl)-2-(hydroxymethyl)-5H-pyrido[3,4-b][1,4]benzothiazin-3(2H)-one (3.1 mmol.) in 20 ml. of pyridine. After stirring for 35 minutes, the reaction mixture was poured onto ice-water and allowed to stand for 16 hours at room temperature, resulting in formation of a yellow solid, which was collected, washed with water, air-dried, then purified using flash chromatography on silica gel, employing a mixture of 2% ethyl acetate: 98% methylene chloride as the eluent. Fractions containing the product were combined and triturated with ether to yield 7-chloro-4-(4-chlorophenyl)-2-[(2-methyl-1-oxohexyloxy)methyl]-5H-pyrido[3,4-b][1,4]benzothiazin-3(2H)-one as a yellow crystalline solid (1.17 g; 76% yield) having the structural formula,

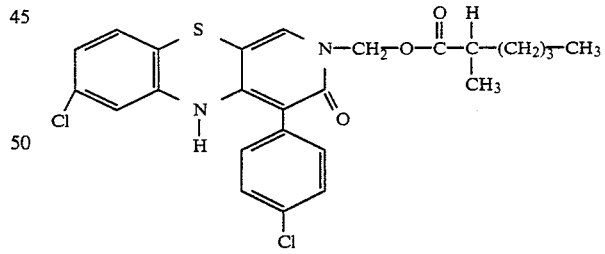

a melting point in the range of 140°-146° C. and the following elemental analysis:

$C_{25}H_{24}N_2O_3SCl_2$: Calculated: C,59.64; H,4.80; N,5.56; Found: C,59.53; H, 4.73; N,5.50.

EXAMPLE 12

A mixture of 1.0 g. of 2,3-dimethylbutyric acid (8.6 mmol.) and 2.5 ml. of thionyl chloride (34.3 mmol.) in 10 ml. of cyclohexane was refluxed on a steam bath for 1.5 hours. The resulting solution was then concentrated under reduced pressure and the residue azeotroped with cyclohexane to yield a colorless oil. The oil was then added dropwise to a cold, suspension containing 0.8 g. of 7-chloro-4-(4-chlorophenyl)-2-(hydroxymethyl)-5H-pyrido[3,4-b][1,4]benzothiazin-3(2H)-one (2.0 mmol.) in 15 ml. of pyridine. After stirring for 35 minutes, the mixture was poured onto ice-water, resulting in the formation of a yellow precipitate which was filtered, washed with water and air-dried, then purified using flash chromatography on silica gel, employing a mixture of 5% ethyl acetate: 95% methylene chloride as the eluent. Fractions containing the product were combined and triturated with ether to yield 7-chloro-4-(4-chlorophenyl)-2-[(2,3-dimethyl-1-oxobutoxy)methyl]-5H-pyrido[3,4-b][1,4]benzothiazin-3(2H)-one as a yellow crystalline solid (110 mg; 11% yield) having the structural formula,

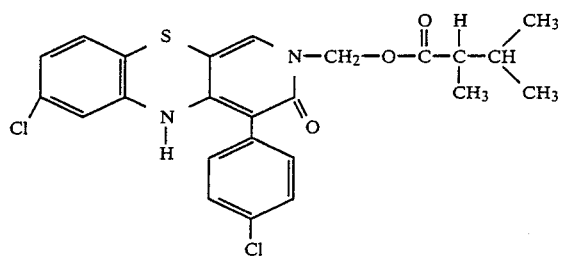

a melting point in the range of 204°–205° C. and the following elemental analysis:

$C_{24}H_{22}N_2O_3SCl_2$: Calculated: C,58.90; H,4.53; N,5.72; Found: C,58.64; H,4.54; N,5.60.

EXAMPLE 13

To 1.0 g. of 7-chloro-4-(4-chlorophenyl)-2-(hydroxymethyl)-5H-pyrido[3,4-b][1,4]benzothiazin-3(2H)-one (2.6 mmol.) in 15 ml. of pyridine at 0° C. was added dropwise 0.9 ml. of hexadecanoyl chloride (3.9 mmol.). After stirring for 35 minutes, the mixture was poured onto ice-water and allowed to stand for 16 hours at room temperature, resulting in the formation of a yellow precipitate. The precipitate was collected, washed with water and air-dried, then purified using flash chromatography on silica gel, employing a mixture of 2% ethyl acetate: 98% methylene chloride as the eluent. Fractions containing the product were combined and triturated with ether to yield 7-chloro-4-(4-chlorophenyl)-2-[(1-oxohexadecyloxy)methyl]-5H-pyrido[3,4-b][1,4]benzothiazin-3(2H)-one as a pale yellow crystalline solid (1.25 g; 78% yield) having the structural formula,

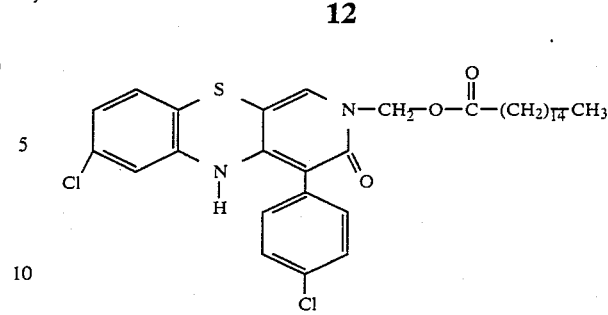

a melting point in the range of 120°–122° C. and the following elemental analysis:

$C_{34}H_{42}N_2O_3SCl_2$: Calculated: C,64.85; H,6.72; N,4.45; Found: C,64.79; H,6.69; N,4.38.

EXAMPLE 14

A mixture of 2.06 g. of 2,3-dimethylvaleric acid (15.8 mmol). in 30 ml. of methylene chloride was cooled in a cold water bath and treated with 2.0 g. of oxalyl chloride (15.8 mmol.). The resulting solution was stirred at room temperature for 2 hours, then the methylene chloride was removed under reduced pressure. The resulting residue was added dropwise to a cold, stirred suspension of 1.2 g. of 7-chloro-4-(4-chlorophenyl)-2-(hydroxymethyl)-5H-pyrido[3,4-b][1,4]benzothiazin-3(2H)-one (3.1 mmol.) in 25 ml. of pyridine. After stirring for 35 minutes, the mixture was poured onto ice-water and allowed to stand for 16 hours at room temperature, resulting in the formation of a yellow precipitate, which was collected, washed with water, air-dried, then purified using flash chromatography on silica gel, employing a mixture of 5% ethyl acetate: 95% methylene chloride as the eluent. Fractions containing the product were combined and triturated with ether to yield 7-chloro-4-(4-chlorophenyl)-2-[(2,3-dimethyl-1-oxopentoxy)methyl]-5H-pyrido[3,4-b][1,4]benzothiazin-3(2H)-one as a pale yellow crystalline solid (1.18 g; 76% yield) having the structural formula,

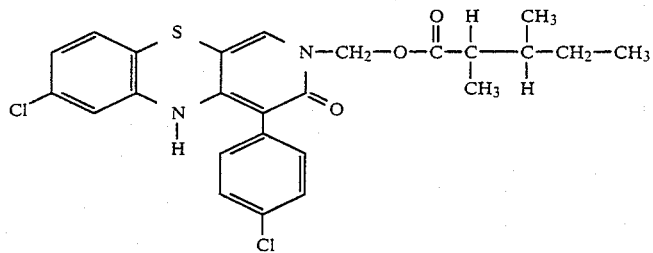

a melting point in the range of 165°–173° C. and the following elemental analysis:

$C_{25}H_{24}N_2O_3SCl_2$: Calculated: C,59.64; H,4.80; N,5.56; Found: C,59.80; H,4.78; N,5.60.

EXAMPLE 15

To 2.0 g. of 7-bromo 4-(4-chlorophenyl)-5H-pyrido[3,4-b][1,4]benzothiazin-3(2H)-one (4.9 mmol.) in 20 ml. dimethylformamide was added 12 ml. of a 5% sodium hydroxide solution (15.0 mmol.) and the resulting suspension was heated on a steam bath until a solution formed. To the solution was then added 20 ml. of a 36% formaldehyde solution (24.0 mmol.), and the resulting reaction mixture was heated until a yellow precipitate formed. The hot reaction mixture was filtered, and the precipitate was washed well with water and dried under high vacuum at room temperature to yield 7-bromo-4-(4-chlorophenyl)-2-(hydroxymethyl)-5H-pyrido[3,4-b][1,4]benzothiazin-3(2H)-one as a yellow powder (1.1 g,; 51% yield) having the structural formula,

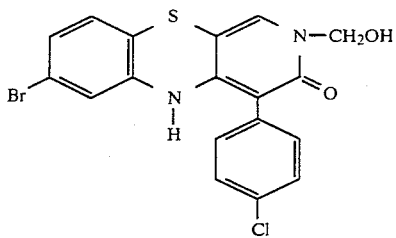

a melting point of 182° C. (with decomposition) and the following elemental analysis:

$C_{18}H_{12}N_2O_2SClBr$: Calculated: C,49.61; H,2.78; N,6.43; S,7.36; Cl,8.14; Br,18.34; Found: C,49.38; H,2.71; N,6.51; S,7.38; Cl,7.95; Br,18.42.

EXAMPLE 16

To 1.0 g. of 7-trifluoromethyl-4-(4-chlorophenyl)-5H-pyrido[3,4-b][1,4]benzothiazin-3(2H)-one (2.5 mmol.) in 10 ml. dimethylformamide was added 6.0 ml. of a 5% sodium hydroxide solution (7.5 mmol.), and the resulting suspension was heated on a steam bath until a solution formed. To the solution was then added 10 ml. of a 36% formaldehyde solution (12.0 mmol.), and the resulting reaction mixture was heated until a yellow precipitate formed. The hot reaction mixture was filtered, and the precipitate was washed with water and dried under high vacuum at room temperature to yield 7-trifluoromethyl-4-(4-chlorophenyl)-2-(hydroxymethyl)-5H-pyrido[3,4-b][1,4]benzothiazin-3(2H)-one as a yellow powder (1.0 g.; 94% yield) having the structural formula,

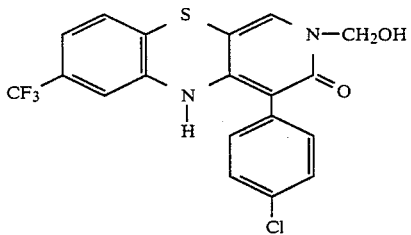

a melting point of 204° C. (with decomposition) and the following elemental analysis:

$C_{19}H_{12}N_2O_2SClF_3$: Calculated: C,53.71; H,2.85; N,6.60; Cl,8.35; F,13.42; Found: C,53.59; H,2.68; N,6.54; Cl,8.57; F,13.47.

EXAMPLE 17

Male Sprague-Dawley derived rats, Charles River Breeders (Portage, MI), weighing between 200–400 grams at the time of testing, were employed in the food intake studies and water intake studies. The rats were housed individually and kept on a 12 hour light-dark light cycle. The room temperature ranged between 23°–25° C.

Food Intake Studies

The rats employed in food intake testing were food deprived on the day preceding testing and were divided into experimental groups that were matched on the basis of average daily food intake and body weight. At approximately 24 hours post-deprivation, the rats were administered a test sample containing as the active ingredient a compound of the present invention. All test samples employed herein were prepared and homogenized in a vehicle of normal saline (to which a few drops of PG/Tween 80 was added). The test samples were administered at an injection volume of 2 ml./kg, unless otherwise stated. Thirty minutes following administration of the test samples, pre-weighed food jars, containing ground meal, were placed in the rats' cages. (Prior to testing the rats were given ground meal for a minimum of 3 days to familiarize the rats with this food.) After 1, 2 and 6 hours of food access, the jars were removed, weighed and returned to the rats' cages providing a 1, 2 and 6 hour intake measurement. The results obtained are represented in Table I. A student t test was used for making statistical comparisons, and the p-values are based upon two-tailed comparisons. The compound employed as the active ingredient of the test sample is indicated by the example number which describes its preparation.

TABLE I

| | Food Intake Test Results | | | | |
|---|---|---|---|---|---|
| Active Ingredient | Dose & Route | n | \multicolumn{3}{c}{Food Intake % of control} |
| | | | 1 Hr. | 2 Hr. | 6 Hr. |
| Example 1 | 10.0 mg/kg i.g. | 12 | 109.8 | 104.5 | 92.1 |
| Example 1 | 32.0 mg/kg i.g. | 12 | 90.2 | 86.6 | 86.5[2] |
| Example 2 | 1.0 mg/kg i.p. | 10 | 87.9 | 90.9 | 100.0 |
| Example 2 | 3.2 mg/kg i.p. | 10 | 57.6[1] | 76.6[2] | 91.0 |
| Example 2 | 10.0 mg/kg i.p. | 10 | 39.4[1] | 61.0[1] | 88.1 |
| Example 2 | 32.0 mg/kg i.p. | 10 | 30.3[1] | 40.3[1] | 70.3[1] |
| Example 2 | 10.0 mg/kg i.g. | 12 | 85.7 | 93.6 | 92.5 |
| Example 2 | 32.0 mg/kg i.g. | 12 | 57.1[1] | 74.4[1] | 87.9[3] |
| Example 3 | 32.0 mg/kg i.g.[4] | 12 | 83.3 | 100.0 | 111.5 |
| Example 3 | 75.0 mg/kg i.g.[4] | 12 | 68.5[2] | 96.8 | 102.6 |
| Example 5 | 75.0 mg/kg i.g. | 9 | 89.9 | 96.1 | 83.1[3] |
| Example 9 | 10.0 mg/kg i.g. | 12 | 111.1 | 102.6 | 96.3 |
| Example 9 | 32.0 mg/kg i.g. | 12 | 111.1 | 106.4 | 92.5 |

[1] $p < .01$ compared with saline control
[2] $p < .05$ compared with saline control
[3] $.05 < p < .09$ compared with saline control
[4] test sample was administered at an injection volume of 3.0 ml./kg

Water Intake Studies

The rats employed in water intake testing were water deprived for 1 day and then maintained on a restricted water schedule. Water was available for two hours on the first day post water deprivation and for 1 hour each day afterwards for a minimum of 1 week. Using drinking tubes (50 ml. graduated cylinders), water intake was measured for at least 3 consecutive days prior to testing. On the day preceding testing, rats were divided into different experimental groups that were matched on the basis of avg. 0–15 min. water intake and body weight. On the day of testing, a test sample, containing as the active ingredient the compound prepared in Example 2, was administered. The drinking tube was introduced to the rats thirty minutes following administration of the test sample, and water intake measurements were taken at intervals of 15, 30, 60 and 120 minutes. Food was removed from the animal at the start of the drinking test. The results obtained are represented in Table II. A student t test was used for making statistical comparisons, and the p-values are based upon two-tailed comparisons.

TABLE II
Water Intake Test Results

| Active Ingredient | Dose (mg/kg) | Route | Water Intake as a % of Control (m = minutes) | | | | |
|---|---|---|---|---|---|---|---|
| | | | 15 m | 30 m | 45 m | 60 m | 120 m |
| Example 2 | 10.0 | i.g. | 96.4 | 98.3 | 99.2 | 100.0 | 103.7 |
| | 18.0 | i.g. | 89.2 | 89.1 | 88.6 | 92.0 | 94.8 |
| | 32.0 | i.g. | 64.9[1] | 69.7[1] | 70.7[1] | 75.2[2] | 79.3[2] |

[1] $p < .01$ compared with saline control
[2] $p < .05$ compared with saline control The above results indicate that certain compounds of the present invention are effective anorectic agents. In addition, compounds of Examples 1, 2 and 3 possess oral appetite suppressant activity. Furthermore, in addition to the above illustrated anorectic activity, the compounds of the present invention also possess other pharmoceutical activity. For example, the compounds of the present invention have an affinity for the benzodiazepine receptor which is associated with clinical utility in the treatment of conditions such as anxiety, convulsions, muscle spasm and the like.

Although this invention has been described with respect to specific modification, the details thereof are not to be construed as limitations, for it will be apparent that various equivalents, changes and modification may be resorted to without departing from the spirit and scope thereof and it is understood that such equivalent embodiments are intended to be included therein.

What is claimed is:

1. A compound of the formula

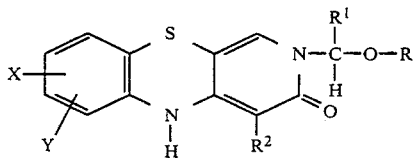

wherein
R is hydrogen or a

group wherein $R^3$ is $C_1$–$C_{15}$ alkyl;
$R^1$ is hydrogen or $C_1$–$C_3$ alkyl;
$R^2$ is phenyl or substituted phenyl containing one or two substituents selected from the class consisting of halo, hydroxy, trifluoromethyl, methoxy, cyano and $C_1$–$C_4$ alkyl; and
X and Y are independently hydrogen, halo, nitro, trifluoromethyl, amino or $C_1$–$C_4$ alkoxy.

2. A compound according to claim 1 wherein $R^2$ is halophenyl.

3. A compound according to claim 2 wherein X is hydrogen.

4. A compound according to claim 3 wherein $R^1$ is hydrogen.

5. A compound according to claim 4 wherein Y is hydrogen.

6. A compound according to claim 5 wherein $R^2$ is 4-chlorophenyl.

7. A compound according to claim 6 wherein the compound is 4-(4-chlorophenyl)-2-(hydroxymethyl)-5H-pyrido[3,4-b][1,4]benzothiazin-3(2H)-one.

8. A compound according to claim 6 wherein R is a

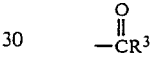

group.

9. A compound according to claim 8 wherein $R^3$ is $C_1$–$C_4$ straight chain alkyl.

10. A compound according to claim 9 wherein the compound is 4-(4-chlorophenyl)-2-[(1-oxobutoxy)methyl]-5H-pyrido[3,4-b][1,4]benzothiazin-3(2H)-one.

11. A compound according to claim 9 wherein the compund is 4-(4-chlorophenyl)-2-[(1-oxopentoxy)methyl]-5H-pyrido[3,4-b][1,4]benzothiazin-3(2H)-one.

12. A compound according to claim 4 wherein Y is chloro.

13. A compound according to claim 12 wherein the compound is 7-chloro-4-(4-chlorophenyl)-2-(hydroxymethyl)-5H-pyrido[3,4-b][1,4]benzothiazin-3(2H)-one.

* * * * *